(12) United States Patent  
Christie

(10) Patent No.: US 11,684,268 B2  
(45) Date of Patent: Jun. 27, 2023

(54) DETECTION DEVICE

(71) Applicant: CALCIVIS LIMITED, Edinburgh Lothian (GB)

(72) Inventor: Adam Christie, Edinburgh Lothian (GB)

(73) Assignee: Calcivis Limited, Edinburg Lothian (GB)

( * ) Notice: Subject to any disclaimer, the term of this patent is extended or adjusted under 35 U.S.C. 154(b) by 896 days.

(21) Appl. No.: 16/505,138

(22) PCT Filed: Jan. 9, 2018

(86) PCT No.: PCT/GB2018/050054  
§ 371 (c)(1),  
(2) Date: Jul. 8, 2019

(87) PCT Pub. No.: WO2018/127717  
PCT Pub. Date: Jul. 12, 2018

(65) Prior Publication Data  
US 2020/0093371 A1    Mar. 26, 2020

(30) Foreign Application Priority Data  
Jan. 9, 2017    (GB) ...................................... 1700317

(51) Int. Cl.  
*A61B 5/00*    (2006.01)

(52) U.S. Cl.  
CPC .......... *A61B 5/0088* (2013.01); *A61B 5/0071* (2013.01); *A61B 5/4547* (2013.01); *A61B 5/682* (2013.01); *A61B 2560/0285* (2013.01); *A61B 2560/0443* (2013.01)

(58) Field of Classification Search  
CPC ... A61B 5/0088; A61B 5/0071; A61B 5/4547; A61B 5/682; A61B 2560/0285; A61B 2560/0443; A61B 2560/0233  
See application file for complete search history.

(56) References Cited

U.S. PATENT DOCUMENTS

| 3,716,170 A | 2/1973 | Mangels |
| 4,184,196 A | 1/1980 | Moret et al. |
| 4,290,433 A | 9/1981 | Alfano |

(Continued)

FOREIGN PATENT DOCUMENTS

| CN | 1231590 A | 10/1999 |
| CN | 2562728 Y | 7/2003 |

(Continued)

OTHER PUBLICATIONS

Search Report dated Nov. 21, 2013 from the European Patent Office in Application No. 11758542.2.

(Continued)

*Primary Examiner* — Chu Chuan Liu  
(74) *Attorney, Agent, or Firm* — Ostrager Chong Flaherty & Broitman P.C.

(57) ABSTRACT

A detection device for active dental caries and/or tooth erosion, comprising a light detection means, fluid dispensing means, and an atomiser, wherein the fluid dispensing means and atomiser are in fluid communication such that a disclosing fluid contained within the fluid dispensing means is dispensed through the atomiser evenly onto a surface of interest.

41 Claims, 13 Drawing Sheets

(56) References Cited

U.S. PATENT DOCUMENTS

| | | | |
|---|---|---|---|
| 4,757,381 A * | 7/1988 | Cooper | H04N 5/2256 |
| | | | 433/116 |
| 5,240,697 A | 8/1993 | Norfleet | |
| 5,342,196 A | 8/1994 | Van Hale | |
| 5,409,835 A | 4/1995 | Lakowicz | |
| 5,604,198 A | 2/1997 | Poduslo et al. | |
| 5,810,863 A * | 9/1998 | Wolf | A61B 17/3417 |
| | | | 606/167 |
| 6,769,911 B2 | 8/2004 | Buchalla et al. | |
| 7,175,430 B1 | 2/2007 | Gasser | |
| 7,601,805 B2 | 10/2009 | Foti et al. | |
| 7,858,394 B2 | 12/2010 | Wunder | |
| 8,647,119 B1 | 2/2014 | Nagai | |
| 9,327,896 B2 * | 5/2016 | Chiba | B01L 3/0227 |
| 2002/0000494 A1 | 1/2002 | Bryan | |
| 2003/0076605 A1 * | 4/2003 | Shohet | A61B 1/247 |
| | | | 359/882 |
| 2003/0175807 A1 | 9/2003 | Baubet et al. | |
| 2004/0191884 A1 | 9/2004 | Isobe et al. | |
| 2005/0003323 A1 | 1/2005 | Katsuda et al. | |
| 2005/0026103 A1 | 2/2005 | Wasylucha | |
| 2005/0273867 A1 | 12/2005 | Brulet et al. | |
| 2005/0283058 A1 | 12/2005 | Choo-Smith et al. | |
| 2005/0287490 A1 | 12/2005 | Stookey et al. | |
| 2006/0099548 A1 | 5/2006 | Rizoiu | |
| 2006/0127327 A1 | 6/2006 | Shi | |
| 2007/0031776 A1 | 2/2007 | Sakaguchi | |
| 2007/0082317 A1 | 4/2007 | Chuang | |
| 2008/0038686 A1 | 2/2008 | Nagai | |
| 2008/0082000 A1 | 4/2008 | Thoms | |
| 2008/0160477 A1 | 7/2008 | Stookey et al. | |
| 2008/0288007 A1 | 11/2008 | Malak | |
| 2010/0034750 A1 | 2/2010 | Perfect et al. | |
| 2010/0239996 A1 | 9/2010 | Ertl | |
| 2011/0200959 A1 | 8/2011 | Rizoiu et al. | |
| 2013/0189641 A1 * | 7/2013 | Perfect | A61B 1/247 |
| | | | 433/29 |
| 2013/0323671 A1 | 12/2013 | Dillon | |
| 2013/0323672 A1 | 12/2013 | Monty et al. | |

FOREIGN PATENT DOCUMENTS

| | | |
|---|---|---|
| CN | 101076295 A | 11/2007 |
| CN | 201175518 Y | 1/2009 |
| CN | 101478931 A | 7/2009 |
| CN | 103153166 A | 6/2013 |
| CN | 105212884 | 1/2016 |
| DE | 19926728 A1 | 12/2000 |
| EP | 1252859 A2 | 10/2002 |
| EP | 1686379 A1 | 8/2006 |
| EP | 1693021 A1 | 8/2006 |
| EP | 1700865 A1 | 9/2006 |
| GB | 2036557 A | 7/1980 |
| JP | 10236914 A | 9/1998 |
| JP | H11244236 A | 9/1999 |
| JP | 2004077217 A | 3/2004 |
| JP | 2004156017 A | 6/2004 |
| JP | 2015118420 A | 5/2005 |
| JP | 2005168463 | 6/2005 |
| JP | 2005168520 A | 6/2005 |
| JP | 2005304600 A | 11/2005 |
| JP | 2006503618 A | 2/2006 |
| JP | 2009518139 A | 5/2009 |
| WO | 9812981 | 4/1998 |
| WO | 0071565 A2 | 11/2000 |
| WO | 200112237 A1 | 2/2001 |
| WO | 200192300 A2 | 12/2001 |
| WO | 2003082904 A2 | 10/2003 |
| WO | 2005025528 A1 | 3/2005 |
| WO | 2006010004 A2 | 1/2006 |
| WO | 2006023424 A2 | 3/2006 |
| WO | 2007038683 A2 | 4/2007 |
| WO | 2007123880 A2 | 11/2007 |
| WO | 2008001303 | 1/2008 |
| WO | 2008075081 A2 | 6/2008 |
| WO | 2008113493 A1 | 9/2008 |
| WO | 2010023582 A1 | 3/2010 |
| WO | 2010136776 | 12/2010 |
| WO | 2012007769 A1 | 1/2012 |
| WO | 2013109978 A1 | 7/2013 |

OTHER PUBLICATIONS

Notice of Reasons for Rejection dated Mar. 3, 2015 from Japanese Patent Office in Application No. 2013-519161.
Final Office Action dated May 10, 2019 in U.S. Appl. No. 13/810,141.
Office Action dated Sep. 16, 2021 from China National Intellectual Property Administration in corresponding China Application No. 201880014017.9.
International Search Report in PCT/GB2018/050054 dated May 28, 2018.
PCT Written Opinion in PCT/GB2018/050054 dated May 28, 2018.
Search Report dated Nov. 17, 2015 from the China Patent Office in Application No. 201180034824.5.
Chinese Equivalent Application 200780051625.9 Rejection Decision dated May 23, 2013 and English translation.
Hay, DI et al. "Equilibrium dialysis and ultrafiltration studies of calcium and phosphate binding by human salivary proteins. Implications for salivary supersaturation with respect to calcium phosphate salts" Calcif Tissue Int. 1982; 34(6):531-8 (Abstract Only) cited in response to CN rejection.
Esser, D. et al.; Sample Stability and Protein Composition of Saliva: Implications for Its Use as a Diagnostic Fluid Biomarker Insights 2008:3 25-37.
Material Safety Data Sheet—BAPTA—cited in response to Chinese rejection.
Zhong, F. et al., "Bcl-2 differentially regulates Ca 2+ signals according to the strength of T cell receptor activation" Journal of Cell Biology 2006: 172(1) 127-137.
Gorokhovatsky, AY et al., "Fusion of Aequorea victoria GFP and aequorin provides their Ca2+ induced interaction that results in red shift of GFP absorption and efficient bioluminescense energy transfer" J. Biochemical and Biophysical Research Communications 2004: 320 703-711.
Baubet et al., "Chimeric green flourescent protein-aequorin as bioluminescent Ca21 reporters at the single-cell level", PNAS, vol. 97, No. 13, pp. 2760-7265, Jun. 20, 2020. (Year: 2020).
Translation of Office Action dated Jun. 14, 2012 for corresponding Japanese patent application No. JP2009-542225.
Translation of second Office Action dated Sep. 13, 2012 for corresponding Chinese patent application No. 2007800516259.
Amaechi, B.T. et al., "Factors affecting the development of carious lesions in bovine teeth in vitro," Archives of Oral Biology, 1998, vol. 43, pp. 619-628, Elsevier Science Ltd.
Callan, J.F. et al. "Switching between molecular switch types by module rearrangement: CA2+enabled, H+ driven 'Off-On-Off', H+driven Yes and Pass 0 as well as H+, Ca2+ driven and logic operations," Chem. Commun., 2004 pp. 2048-2049, The Royal Society of Chemistry 2004, U.K.
Charbonneau, H. et al., "Amino Acid Sequence of the Calcium-Dependent Photoprotein Aequorin," Biochemistry, 1985, vol. 24, pp. 6762-6771, American Chemical Society, Washington, D.C.
Fagan, T.F., et al., "Cloning, expression and sequence analysis of cDNA for the Ca2+binding photoprotein, mitrocomin," Federation of European Biochemical Societies, vol. 333, No. 3, pp. 301-305, Elsevier Science Publishers B.V.
Head, James F. et al., "The crystal structure of the photoprotein aequorin at 2.3A resolution," Nature, vol. 405, pp. 372-376, May 18, 2000, Macmillan Magazines Ltd.
Hemingway, C.A., et al. "Enamel erosion by soft drinks with and without abrasion," British Dental Journal, vol. 201, No. 7, p. 439, Oct. 7, 2006.
Illarionov, B.A. et al., "Cloning and expression of the cDNA of the Calium-Activated photoprotein obeline from hydroid polypobelia longissima," Proceedings of the Academy of Sciences, 1992, vol. 326, No. 5, UDC 575 113. Genetics, Russia.

(56) References Cited

OTHER PUBLICATIONS

Illarionov, B.A., et al., "Sequence of the CDNA encoding the Ca2+ activated photoprotein obelin from the hydroid polyp Obelia longissima," Gene, vol. 153, pp. 273-274, 1995, Elsevier Science B.V.

Inouye, S. et al., "Cloning and sequence analysis of cDNA for the Ca2+activated photoprotein, clytin," Federation of European Biochemical Societies, vol. 315, No. 3, pp. 343-346, 1993, Elsevier Science Publishers B.V.

Inouye, S. et al., "Cloning and sequence analysis of cDNA for the luminescent protein aequorin," Proceedings of the National Academy of Sciences, USA, Biochemistry, vol. 82, pp. 3154-3158, May 1985.

Kim, T-H, et al., "A Fluorescent Self-Amplifying Wavelength-Responsive Sensory Polymer for Fluoride Ions," Angew, Chem. Int. Ed. 2003, vol. 42, pp. 4803-4806, Wiley-VCH Verlag GmbH & Co. KGaA, Weinheim, Germany.

Markova, S.V. et al., "Obelin from the Bioluminescent Marine Hydroid Obelia geniculata: Cloning, Expression, and Comparison of Som Properties with Thise of Other Ca2+Regulated Photoproteins," Biochemistry 2002, vol. 41, pp. 2227-2236, American Chemical Society, Washington, D.C.

Miyawaki, A. et al., "Fluorescent indicators for Ca2+ based on green fluorescent proteins and calmodulin," Nature, vol. 388, pp. 882-887, Aug. 28, 1997, Macmillan Publishers Ltd.

Miyawaki, A. et al., "Dynamic and quantitative Ca2+ measurements using improved cameleons," Mar. 1999, Proceedings of the National Academy of Science, USA Cell Biology, vol. 296, pp. 2135-2140.

Nagai, T. et al., "Circularly permuted green fluorescent proteins engineered to sense Ca2+," PNAS, Mar. 13, 2001, vol. 98, No. 6, pp. 3197-3202.

"Strontium and Dental Carries," Nutrition Reviews, vol. 41, No. 11, Nov. 1983.

Prasher, D. et al., "Cloning and expression of the cDNA Coding for aequorin, A Biolluminescent Calcium-Binding Protein," Biochemical and Biophysical Research Communications, vol. 126, No. 3, Feb. 15, 1985, pp. 1259-1268, Academic Press, Inc.

Prasher, D. et al., "Sequence Comparisons of Complementary DNAs Encoding Aequorin Isotypes," Biochemistry 1987, vol. 26, pp. 1326-1332, American Chemical Society, Washington D.C.

Rawls, H.R., "Demonstration of Dye-Uptake as a Potential Aid in Early Diagnosis of Incipient Caries," Caries Res., vol. 12, pp. 69-75 (1978).

Rudolf, R. et al., "Looking Forward to Seeing Calcium," Nature Reviews / Molecular Cell Biology, vol. 4, Jul. 2003, pp. 570-586.

Shimomura, O., et al., "Halistaurin, phialidin and modified forms of aequorin as Ca2+ indicator in bioloical systems," Biochem J. (1985) vol. 228, lines 745-749, Great Britain.

Shimomura, O., et al., The discovery of aequorin and green fluorescent protein, Journal of Microscopy, vol. 217, Pt. 1, Jan. 2005, pp. 3-15, The Royal Microscopical Society.

Shimomura, O., et al., "Peroxidized coelenterazine, the active group in the photoprotein aequorin," Proceedings of the National Academy of Science USA/ Biochemistry, vol. 75, No. 6, pp. 2611-2615, Jun. 1978.

Thorpe, J.H. et al., "Conformational and hydration effects of site-selective Sodium, Calcium and Strontium Ion binding to the DNA Holliday Junction Structure d(TCGGTACCGA)," Journal of Molecular Biology (2003) vol. 327, lines 97-109, Elsevier Science Ltd.

Tsuji, F.I., et al., "Molecular Evolution of the Ca2+binding photoprotein if the hydroza," Photochemistry and Photobiology, vol. 62, No. 4, pp. 657-661, 1995 American Society for Photobiology, U.S.

Ward, W.W., et al., "Properties of Mnemiopsin and Berovin, Calcium-Activated Photoproteins from the Ctenophores *Mnemiopsis* sp. and *Beroe ovata*," Biochemistry, vol. 13, No. 7, 1994.

Pouls (The Townsend Letter for Doctors and Patients, EDTA Chelation Therapy, Jul. 31, 1999, http://www.townsendletter.com/Chelation/chelation_extreme.htm, pp. 1-28) (Year: 1999).

http://en.wikipedia.org/wiki/Prism pdf retrieved Jun. 13, 2014.

The Second Office Action, Application No. 201880014017.9, dated Feb. 8, 2022.

Notification of Grounds of refusal, Patent Application No. 2019-557689, dated Feb. 8, 2022.

Rejection Decision in China Application No. 201880014017.9, dated Sep. 8, 2022 from the China Patent Office.

Communication pursuant to Article 94(3) EPC in Application No. 18 708 168.2-1113, dated Oct. 10, 2022 from the European Patent Office.

Notification of grounds of refusal in Japanese Application No. 2019-557689, dated Jan. 31, 2022 from the Japanese Patent Office.

\* cited by examiner

DETECTION DEVICE

TECHNICAL FIELD

The present invention relates to an intra-oral detection device. More particularly, the present invention relates to an intra-oral detection device for detecting tooth demineralization.

BACKGROUND

Many dental problems result from tooth demineralization. Demineralization is an underlying process involved in the development of dental caries, tooth erosion and dentine hypersensitivity. Demineralization of one or more of the dental hard tissues causes a loss of tooth integrity. Minerals are generally present in the dental hard tissues in a mineralized state and demineralization involves the release of free ions.

Dental caries lesions damage the structure of teeth. The disease dental caries can lead to pain, infection, bad breath, foul tastes and tooth loss. In severe cases, infection can spread to the surrounding soft tissues, which can result in death. Factors inducing caries include bacteria, which collect around teeth in a sticky mass known as plaque, and ingested food and drink. The bacteria associated with early demineralization are *Streptococcus mutans*, while lactobacilli appear to be related to lesion progression. These bacteria convert sugars in food/drink into acids, such as lactic acid, through fermentation, and, if left in contact with teeth, these acids cause demineralization.

SUMMARY

Dental erosion is a progressive loss of hard tissue thickness incrementally from the tooth surface and is frequently caused by acidic drinks/foods (which may or may not be sugary), which cause demineralization and can lead to exposure of the dentine. Erosion can also be accelerated by tooth-brushing of acid-softened enamel (or dentine), leading to the complete removal of enamel and consequent exposure of dentine. Specifically, erosion refers to non-bacterial processes causing progressive loss of hard dental tissue. Tooth erosion occurs when the enamel on your teeth is worn away by acid.

Dentine hypersensitivity is the pain arising from exposed dentine, typically in response to external stimuli (and which cannot be explained by any other form of dental disease). The exposed open dentinal tubules lead directly to pulp tissues, which include the nerves within it.

Initial caries diagnosis involves inspection of all visible tooth surfaces, often using a dental explorer, or metal pick, and mirror, illuminated by a bright light source. In some cases, the sign of a carious lesion or of demineralization of enamel is the appearance of a chalky white spot on the surface of a tooth. However such a spot is not always visible.

A common technique to aid the early diagnosis of caries is to blow air across the suspect surface. As it continues to demineralize, caries may turn brown and eventually develop into a cavity. Large caries lesions are often visible to the naked eye. However, smaller lesions can be very difficult to identify. Often active caries will remain undetected until late in the process and significant damage has been done to the integrity of the tooth. Sometimes it is only when the patient starts to feel pain that an X-ray is used to confirm the presence of caries. Once a cavity forms, the lost tooth structure cannot be regenerated. The process before this point is potentially reversible, therefore it is essential to identify caries as soon as possible.

Erosion is detected by visual inspection, as for caries detection. Signs and symptoms that indicate erosion include increased transparency of incisors, fillings raised above the surrounding teeth, and wear on non-biting surfaces.

Dentine hypersensitivity will be reported by the patient and investigated by a dentist. Useful diagnostic tools are the air/water syringe, dental explorer, percussion testing, bite stress tests, and other thermal tests such as an ice cube and assessment of occlusion. However, these methods, based on the patient's report, are subjective and lack accuracy.

If caries, tooth erosion or hypersensitive teeth can be identified early, then treatment can be applied and teeth protected. For example, problem areas may be sealed to prevent further demineralization. Early detection and diagnosis are therefore paramount.

Many devices have been developed to aid detection of tooth demineralization. One example is described in US20050003323A1. The device described comprises an intraoral camera and an illuminating light. The illuminating light is adapted to shine excitation light, infrared light, or ultraviolet light onto the surface of a tooth and the intraoral camera adapted to record the images of the tooth under these lights conditions. The device can be used to determine differences in the reflected light due to demineralization. A similar device is described in US2008/0160477. The device in this document uses quantitative light fluorescence to investigate tooth demineralization and an excitation light is used to illuminate the tooth surface. The disadvantage of the devices of US20050003323A1 and US2008/0160477 is that they rely on merely looking at differences in the fluorescent properties of the tooth surface when exposed to light at varying spectrums. These devices may not detect early stage caries due to the fact that at the early stages of caries there may not be a change in the light reflecting properties of a tooth. Importantly, these devices cannot detect if caries is active (and therefore likely to progress) or inactive (and therefore unlikely to progress), a distinction which is key to effective clinical management of caries.

The sooner caries and tooth erosion are detected the more likely it is that the effects can be reversed. As described in applicant's own WO2008075081A2 (the disclosure of which is incorporated by reference), a disclosing solution was developed in order to detect early stage active caries and erosion. This disclosing solution contained an ion dependent photoprotein that emitted an optical signal in the presence of free ions. Chemiluminescent photoproteins that emit a luminescent signal were found to be effective in detecting free ions released from the tooth surface and calcium ion dependent chemiluminescent photoproteins that emit a luminescent signal were found to be the most advantageous in detecting early stage active caries and tooth erosion. The term luminescence in this instance relates to bioluminescence, which is a form of chemiluminescence.

As described in applicant's own WO2012007769A1 (incorporated by reference), a detection device was developed with the intent to detect the optical signal emitted from the disclosing solution of WO2008075081A2 after it had come into contact with free ions released from teeth. It is an object of the invention to seek to provide a further refinement of the device described in WO2012007769A1 and introduce additional advantageous features that allow for more efficient detection of the optical signal emitted from the aforementioned disclosing solution.

In a first aspect of the invention, there is provided a detection device for active dental caries and/or tooth erosion, comprising a light detection means, a fluid dispensing means, and an atomiser, wherein the fluid dispensing means and atomiser are in fluid communication such that a fluid contained within the fluid dispensing means is dispensed through the atomiser onto a surface of interest as a spray. The detection device of the invention is advantageous compared to prior detection devices as it quickly detects an optical light signal emitted from a disclosing solution after it has been applied to a surface of interest. The fluid dispensing means may be used to store a disclosing solution and administer it to the surface of interest via the atomiser. This is advantageous as the atomiser provides for an even distribution of the disclosing solution and allows for the optical signal produced by the disclosing solution to be detected by the detection device. The light detection means may be a camera, charge coupled device (CCD), or complementary metal-oxide semiconductor (CMOS). The light detection means may be specifically adapted to detect a low light luminescent signal produced by the disclosing solution containing a chemiluminescent photoprotein.

Preferably, the detection device further comprises a body portion, comprising a proximal end and a distal end, and an applicator portion. The body portion 7 may be elongate in shape such that is fits easily into the oral cavity of a patient. More preferably, the applicator portion is reversibly removable and couples to the distal end of the body portion. The use of a reversibly removable applicator portion allows this portion of the device to be disposable. A disposable applicator portion is advantageous as is prevents cross contamination between patients.

Preferably, the reversibly removable applicator portion comprises the atomiser. In the context of the present invention, an atomiser is a device for the production of a spray of fine droplets. It is advantageous for the reversibly removable applicator portion to comprise the atomiser as this is the part of the device is disposable and it is the atomiser that expels a disclosing solution into a patient's oral cavity, therefore, potentially becoming contaminated with microbes from the oral cavity.

Preferably, the atomiser has an at least one fluid atomiser channel in fluid communication with at least one fluid outlet. More preferably, the atomiser has a plurality of fluid atomiser channels in fluid communication with a plurality of fluid outlets. The at least one fluid atomiser channel allows passage of a disclosing solution from the fluid dispensing means to the at least one fluid outlet which sprays the disclosing solution as a spray onto a surface of interest.

Preferably, in the embodiment wherein the atomiser has a plurality of fluid outlets, the fluid outlets are adapted to provide a substantially equal flow of fluid therefrom. This is advantageous as the equal flow rate of fluid from the plurality of fluid outlets assists in providing an even distribution of the disclosing solution as a spray to the surface of interest.

Preferably, the reversibly removable applicator portion comprises an applicator housing portion, a reversibly removable combined atomiser and fluid conduit portion, and a reversibly removable light shield or skirt portion. This arrangement is advantageous as it allows at least some of the components to be disposable. For example, the reversibly removable combined atomiser and fluid conduit portion and the reversibly removable light shield or skirt portion may be disposable and the applicator housing portion may be autoclavable. Disposable reversibly removable combined atomiser and fluid conduit portion and reversibly removable light shield or skirt portion is advantageous as it prevents cross-contamination. Also, if the reversibly removable combined atomiser and fluid conduit portion is reused, the it may lead to clogging or blockages in the fluid channels that may prevent the device from working optimally. In addition, a reversibly removable light shield or skirt portion allows different sized light shield/skirts to be used for different surfaces of interest. For example, different light shields or skirts can be used for different sized teeth. Due to the differing nature of the size and shape of teeth, larger or smaller light shields or skirts may need to be used. Also, a slit or gap on both side of the light shield or skirt may be required in order to properly seat the device onto the surface of a tooth.

Preferably, the substantially equal flow of fluid from the plurality of fluid outlets is provided by a first set of fluid outlets in fluid communication via the fluid atomiser channels with a second set of fluid outlets. Having multiple outlets along the same fluid atomiser channel is advantageous as it provides more outlets for the fluid such that it can be evenly distributed onto the surface of interest.

Preferably, the plurality of fluid atomiser channels have a first diameter prior to the first set of fluid outlets and a second diameter after the first set of fluid outlets but prior to the second set of fluid outlets, wherein the second diameter is smaller than the first diameter. This arrangement is advantageous as it allows the fluid to flow to the first outlet and exit the outlet at an optimal flow rate. The fluid channel having a smaller diameter to the second fluid outlets allows the fluid to exit the second outlet at the same or a similar optimal flow rate. This feature is advantageous as if the channel had the same diameter to both of the fluid outlets a Venturi effect would be created and there would be a bias to the second set of fluid outlets and an uneven flow rate.

Preferably, the atomiser comprises a light shield or skirt for minimising ambient light reaching the light detection means. This feature advantageously provides a barrier that reduces the amount of ambient light reaching the light detection means, which may lower the sensitivity of the light detection device to the light emitting from a surface of interest after application of the disclosing solution. More preferably, the light shield or skirt is opaque and is made from a silicone rubber material of a hardness of Shore 20 A to 40 A. Even more preferably, the light shield or skirt is opaque and is made from a silicone rubber material of a hardness of Shore 30 A.

Preferably, the at least one fluid outlet opens into a cavity defined by the interior of the light shield or skirt. This feature is advantageous as it allows the spray produced by the atomiser to be contained within the inner boundary of the light shield or skirt and directed to the surface of interest by the cavity and around the surface of interest, i.e. a tooth, as defined by the light shield or skirt. This prevents disclosing solution from being wasted and ensures even coating of the surface of interest.

Preferably, the reversibly removable applicator portion comprises an applicator housing portion, a clear window portion, a fluid channel portion, and the atomiser. A layered construction reduces the cost of the applicator portion and makes assembly of the application portion more efficient.

Preferably, the clear window portion at least partially protrudes into the cavity defined by the interior of the light shield or skirt to form a deflecting surface. This is advantageous as it aid formation of a fine spray. As the fluid exits the fluid outlets it will hit the deflecting surface causing further atomisation of the fluid to occur. The fluid deflecting surface may be angled to provide optimal deflection and atomisation of the fluid.

Preferably, the clear window portion has an indentation to form a lip. The surface of the clear window portion in the same plane as the surface of interest, for example a tooth, may be indented to prevent the surface being obstructed by the spray as it exits the fluid outlets or when it is deflected by a deflecting surface. The lip formed by indentation advantageously allows light to transit through the clear window portion such that it can be detected by the light detection means. Droplets forming on the surface of the clear window portion would affect the quality of the image recorded by the device and may prevent the device from optimally detecting the light generated by the disclosing substance.

Preferably, all or part of the clear window portion may be frosted. Frosted plastic materials are readily available and can allow the passage of light while also being opaque by varying degrees. Advantageously frosting of the clear window portion has been found to control accumulation and/or flow of fluid across the surface of the clear window portion, while surprisingly not interfering with capturing of an image.

Preferably, the fluid channel portion comprises an enclosure for a fluid orifice of the fluid dispensing means. This is advantageous as it provides a direct interaction between the fluid orifice of the fluid dispensing means and the fluid channel of the applicator portion.

Preferably, the reversibly removable applicator comprises a clip for securing the applicator to the body portion. More preferably, the clip corresponds to a catch on the body portion. This arrangement advantageously secures the reversibly removable applicator to the body portion and allows it to be removed only when the user wishes this to occur. A clip and catch arrangement may be highly advantageous for the safety of the device. If the fluid channel(s) or the outlet(s) of the device become blocked, this arrangement secures the reversibly removable applicator to the body and prevents the applicator from being ejected from the body portion inside a patient's mouth due to a sudden increase in pressure caused by the blockage.

Preferably, the fluid dispensing means includes the disclosing solution. More preferably, the disclosing solution comprises a composition capable of producing an optical signal characteristic of the presence of free ion. Even more preferably, the composition is a calcium dependent photoprotein. In the context of the present invention, a disclosing solution is a fluid that is applied to a surface of interested and produces a signal in the presence of free ions released from that surface. The composition forming the active part of the disclosing solution may be referred to as a disclosing solution. In certain embodiments the disclosing solution may be a liquid or a gel. A disclosing solution that produces a detectable signal in the presence of free ions is highly advantageous as it allows assessment of whether the caries is active or inactive. The major free ion produced by active caries is the calcium ion. A calcium dependent photoprotein provided as part of the disclosing solution is a highly advantageous means of detecting free calcium ions released from teeth. Calcium dependent photoproteins that produce a luminescent flash of light upon contact with calcium ions are highly advantageous. The flash of light produced by the interaction of these proteins with calcium is very brief, in the order of reaching an emission maximum in 10 ms, and a highly sensitive light detection means adapted for the detection of luminescent light is preferred.

Preferably, the fluid dispensing means comprises a syringe. More preferably, the fluid dispensing means further comprises a syringe driver means, wherein the syringe driver means is adapted to actuate the plunger of the syringe and expel liquid contained therein. A syringe advantageously provides a means of dispensing the disclosing solution from the device. A syringe is also easy for a user to use and easy to load into and remove from the device.

In a second aspect of the invention, there is provided a kit for dental caries and/or tooth erosion detection comprising the detection device of the first aspect of the invention.

In the context of the present invention, the proximal end refers to the end of the device proximal the user of the detection device, in contrast to the end of the device that is proximal to a patient when the device is in use on that patient.

BRIEF DESCRIPTION OF THE DRAWINGS

The invention will further be described by way of example and with reference to the accompanying drawings, in which:

FIG. 9b is a cross-sectional view through Section E-E of the applicator portion shown in FIG. 9a;

DETAILED DESCRIPTION OF PREFERRED EMBODIMENTS

Figure 1:
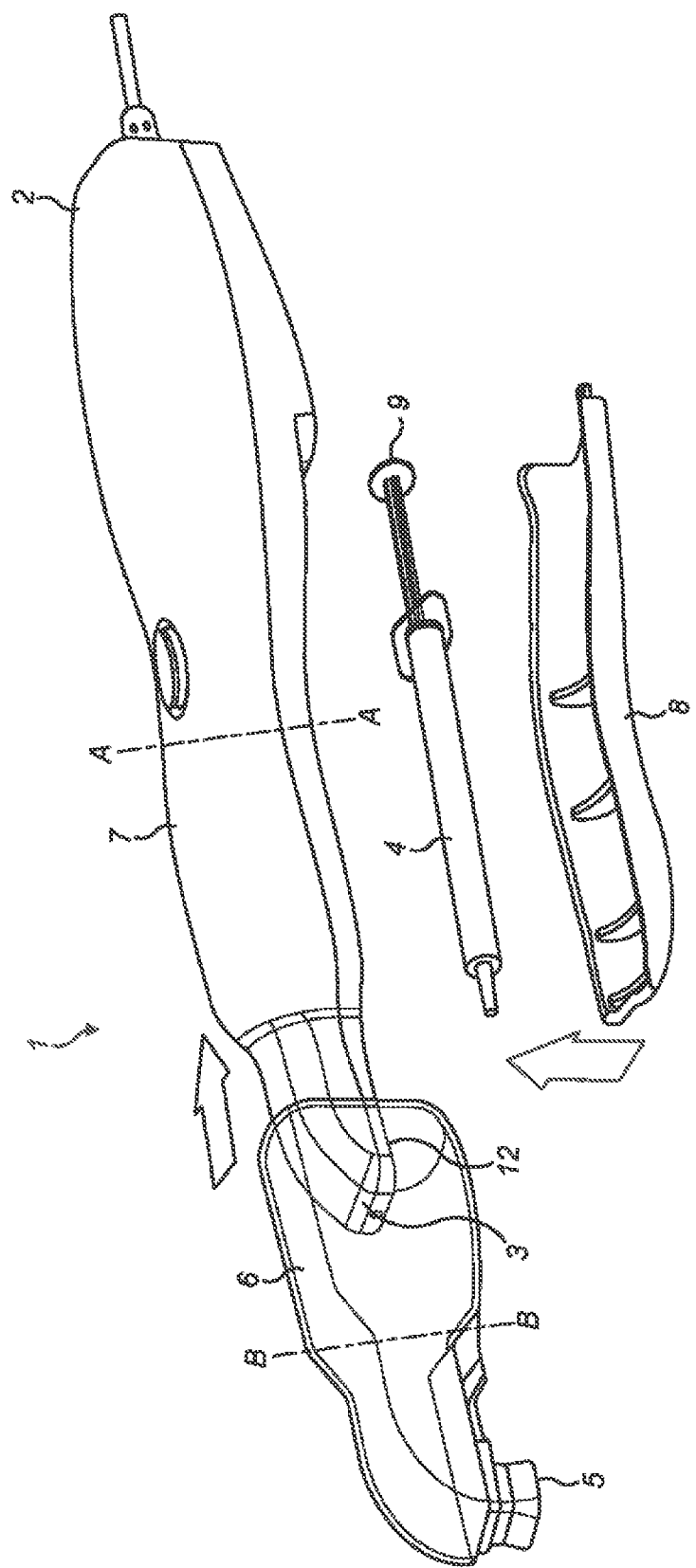
FIG. 1 is a perspective view of one embodiment of the detection device according to the present invention showing the body portion and applicator portion.

Wherever possible the same reference numeral has been used to denoted the same feature in all of the drawings.

One embodiment of the detection device 1 according to the present invention is shown in FIG. 1 and comprises comprising a light detection means 12, fluid dispensing means 4, and an atomiser 5, wherein the fluid dispensing means 4 and atomiser 5 are in fluid communication such that a fluid contained within the fluid dispensing means 4 is dispensed through the atomiser 5 onto a surface of interest as a spray.

FIG. 1 also shows that in some embodiments the detection device may further comprise a body portion 7, which comprises a proximal end 2 and a distal end 3, and a reversibly removable applicator portion 6, wherein the reversibly removable applicator portion 6 reversibly couples to the distal end 3 of the body portion 7. The body portion 7 may be elongate in shape such that is fits easily into the oral cavity of a patient. The body portion 7 may further comprise a cover 8 for the fluid dispensing means 4. Part of the fluid dispensing means 4 may be a syringe 9, as also shown in FIG. 1.

Figure 2:
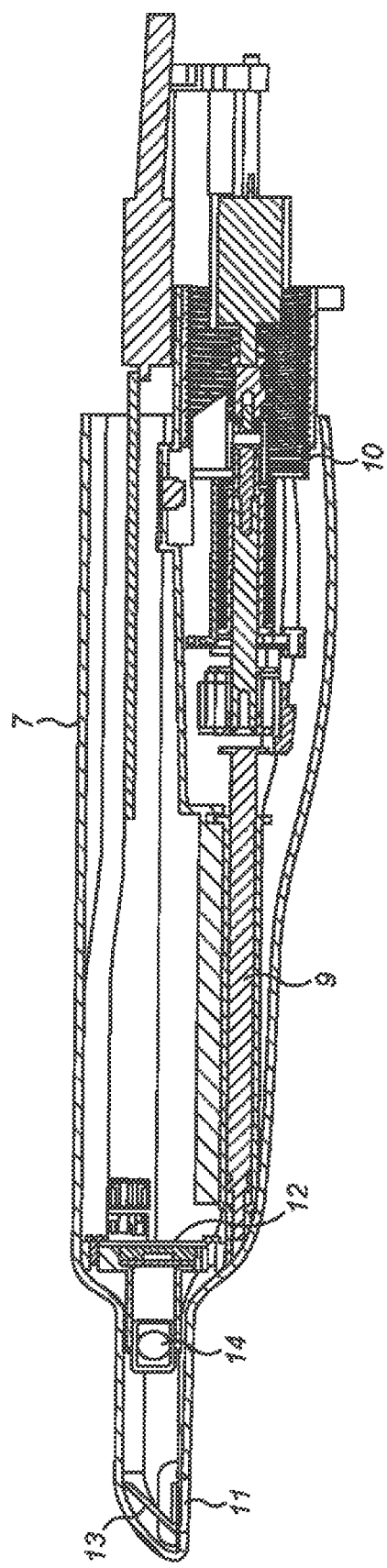
FIG. 2 is a cross-sectional view through Section A-A of one embodiment of the body portion of the detection device shown in FIG. 1.

FIG. 2 shows a cross-sectional schematic of one embodiment of the body portion 7. FIG. 2 shows that in some embodiments the fluid dispensing means 4 may be formed by a syringe 9 and a syringe driver means 10. The syringe driver means 10 may be any means that advances the plunger of the syringe 9. In one embodiment, the syringe driver means 10 may be formed from a compression spring that, upon activation of the device, is compressed and released causing a force to be applied to the plunger of the syringe 9. In this embodiment, the same force is applied to the plunger of the syringe 9 every time the device is activated. The pressure exerted on the plunger by the compression spring may be about 1 to 2 mega Pascal. More preferably, the pressure exerted on the plunger by the compression spring may be about 1.5 mega Pascal. Therefore, substantially the same volume of liquid is expelled from the device every time the device is activated. In certain embodiments, about 1 µl to 1000 µl of liquid is expelled from the fluid dispensing means 4 when the device is activated. In a preferred embodiment, about 10 µl to 40 µl of liquid is expelled from the fluid dispensing means 4 when the device is activated. In a further preferred embodiment, about 20 µl to 30 µl of liquid is expelled from the fluid dispensing means 4 when the device is activated. In yet a further preferred embodiment, about 25 µl of liquid is expelled from the fluid dispensing means 4 when the device is activated. The syringe driver means 10 may further comprise a motor winder means that produces the compressive force to compress the spring. Upon insertion of the syringe 9 into the device, the syringe driver means 10 may perform an action to prime the syringe 9 ready for use. This action may involve expelling any air from the fluid conduits of the device such that the fluid dispensing means 4 is filled only by disclosing solution.

In an alternative embodiment, the fluid dispensing means 4 may comprise a pressurised system for expelling a fluid. In such embodiments, the disclosing solution may be mixed with a propellant.

FIG. 2 also shows the detection apparatus of the device. In this embodiment, the body portion 7 has a transparent window 11 for allowing light from the surface of interest to pass through to the interior of the body portion 7 such that it is detected by a light detection means 12. As light passes through the transparent window 11, it is reflected by mirror 13 and directed through lens array 14 to be recorded by the light detection means 12. In another embodiment not shown in FIG. 2, the light is redirected by a prism. The mirror 13 or prism may be coated with a bandpass, polarising or dichromic filter material. These filter materials may be useful in reducing the signal to noise ratio from the light entering the transparent window 11.

In use, the embodiment of the detection device 1 shown in FIGS. 1 and 2 may be operated by a dental practitioner. First, a syringe 9 containing a disclosing solution may be inserted into the body portion 7. The syringe 9 may be retained within the body portion 7 by reattaching cover 8. The applicator portion 6 may then be placed onto the distal end 3 of the body portion 7. The device may then be inserted into the mouth of a patient and the atomiser 5 placed over a tooth surface of interest. The device may be activated by depression of a trigger on the body portion 7. The fluid dispensing means 4 is then activated. The syringe driver mechanism 10 will apply a force to the plunger of the syringe 9 such that a specified volume of disclosing solution is expelled from the syringe 9. The disclosing solution will pass through a fluid channel and into the atomiser 5. The disclosing solution will be expelled from the atomiser 5 as a fine spray from the fluid outlets of the atomiser 5. The spray will contact a surface of interest and, if there are free ions present on the surface of interest, an optical signal will be detected by the light detection means 12. The light detected may then be used to create an image on an image display device. In some embodiments, the image formed from the detected optical signal emitted from the disclosing solution may be overlaid onto a visible light image of the surface of interest taken by the device prior to application of the disclosing solution using a light source integrated into the device, for example an LED or lamp.

In one embodiment images taken by the device are transmitted to a computer wirelessly. In another embodiment images taken by the device are transmitted to a computer via a cable operably attached to the device and computer.

Figure 3:
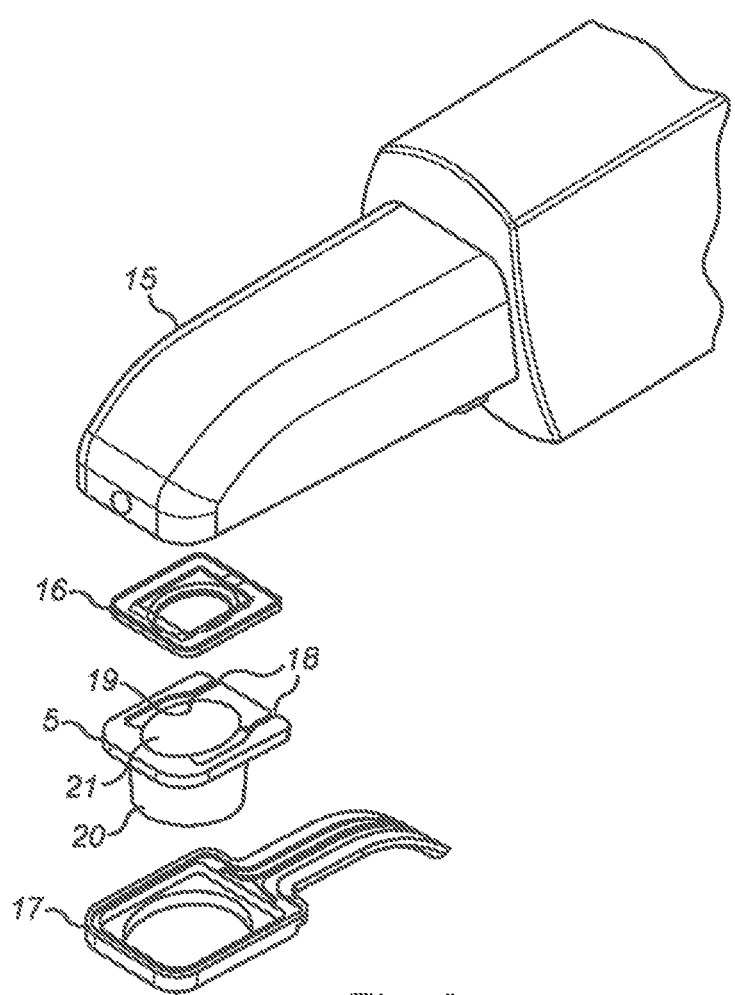
FIG. 3 is an exploded image of the parts of the detection device that form the applicator portion.

FIG. 3 shows one embodiment of the parts that form the reversibly removable applicator portion 6. The reversibly removable applicator portion 6 may comprise an applicator housing portion 15, a clear window portion 16, a fluid conduit portion 17, and the atomiser 5. The fluid conduit portion 17 forms a conduit to place the fluid dispensing means 4 in fluid communication with the atomiser 5. When the fluid dispensing means 4 is activated, fluid will exit the fluid dispensing means 4 along the path defined by the conduit of the fluid channel portion 17 and exit this portion into the atomiser 5. The atomiser 5 may have one or more fluid atomiser channels 18 for receiving the fluid from the fluid conduit portion 17. In the embodiment of FIG. 3, the fluid conduit portion 17 splits the conduit into two separate channels prior to the fluid entering the atomiser 5. The section of the fluid conduit portion 17 that splits into two separate channels may do so around the curved surface of a wall opposite the opening of the fluid conduit. In an alternative embodiment, the fluid enters the atomiser in a single conduit formed by the fluid conduit portion 17 and the conduit is split into two separate channels within the atomiser 5, thereby forming the fluid atomiser channels 18.

In one embodiment, the fluid conduit portion 17 has a proximal end and a distal end that correlate to the orientation of the proximal end 2 and distal end 3 of the body portion 7. The proximal end of the fluid conduit portion 17 forms a conduit for the flow of fluid from the fluid dispensing means 4 to the atomiser 5. The distal end of the fluid conduit portion 17 forms a receptacle for holding the atomiser 5. The atomiser 5 may sit within the receptacle. In one embodiment, the light shield or skirt 20 of the atomiser 5 may sit within a cavity formed in the distal end of the fluid conduit portion 17.

In one embodiment, the clear window portion 16 may be made from acrylic. In one embodiment, the clear window portion 16 is positioned on top of the atomiser 5 such that the clear window portion 16 seals the upper part of the at least one fluid atomiser channel(s) 18. In a preferred embodiment, when the applicator portion 6 is secured to the body portion 7, the clear window portion 16 of the reversibly removable applicator portion 6 corresponds to the transparent window 11 in the body portion 7. Having the clear window portion 16 of the applicator portion 6 in alignment with the transparent window portion 11 of the body portion 7 allows light to pass from the surface of interest to the light detection means 12 unimpeded. In one embodiment, the clear window comprises a coating of an anti-mist composition. The anti-mist composition prevents the clear window portion 16 from misting up due to the breath in the mouth of a patient.

In one embodiment, one or more of the applicator housing 15, clear window portion 16, fluid conduit portion 17, and atomiser 5 are bonded to each other by ultra-sonic welding.

In one embodiment, the atomiser 5 may have at least one fluid atomiser channel 18. In a preferred embodiment shown in FIGS. 4 and 5, the atomiser 5 may have at least two fluid atomiser channels 18. In one embodiment, the fluid atomiser channels 18 lead to at least one fluid outlet 19. In a preferred embodiment, each fluid atomiser channel 18 leads to at least two fluid outlets 19. In the embodiment of FIGS. 4 and 5 each fluid atomiser channel 18 has two fluid outlets 19. In a further embodiment, the fluid atomiser channel(s) 18 have a first diameter prior to the first set of fluid outlets 19a and a second diameter after the first set of fluid outlets 19a but prior to the second set of fluid outlets 19b, wherein the second diameter is smaller than the first diameter.

Figure 4A:
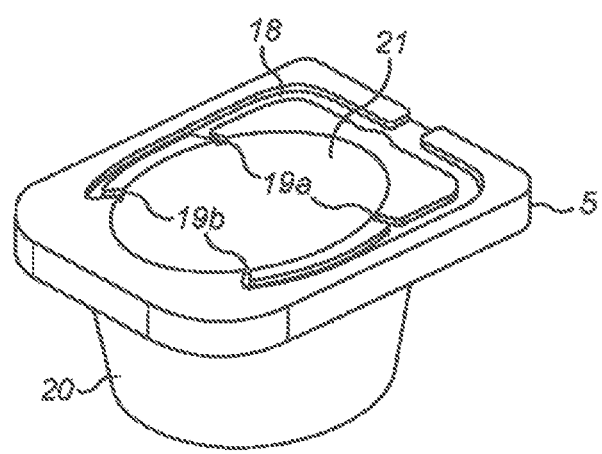
FIG. 4a is a perspective view of the atomiser.
Figure 4B:
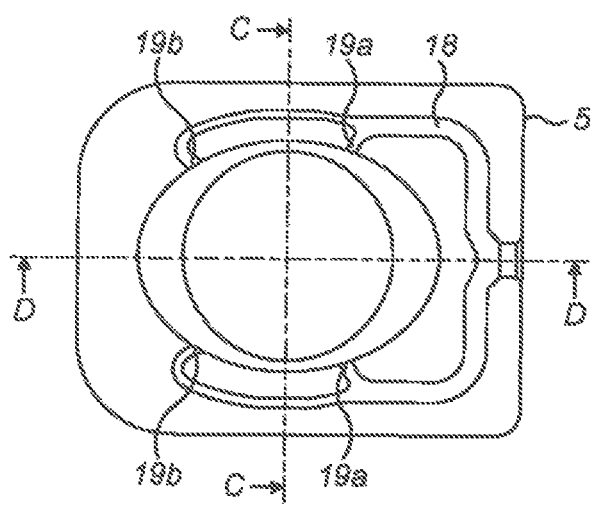
FIG. 4b is a view of the atomiser from above.
Figure 4C:
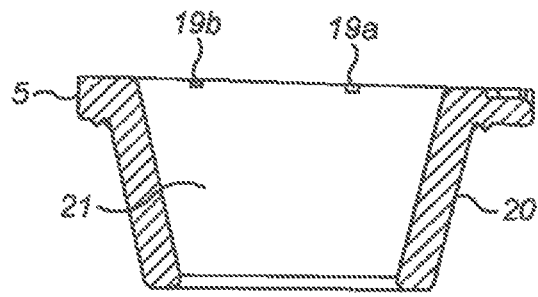
FIG. 4c is a cross-sectional view through Section C-C of the atomiser as marked on FIG. 4b.
Figure 4D:
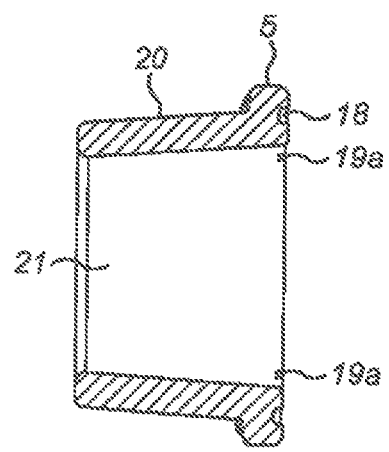
FIG. 4d is a cross-sectional view through Section D-D of the atomiser as marked on FIG. 4b.
Figure 5:
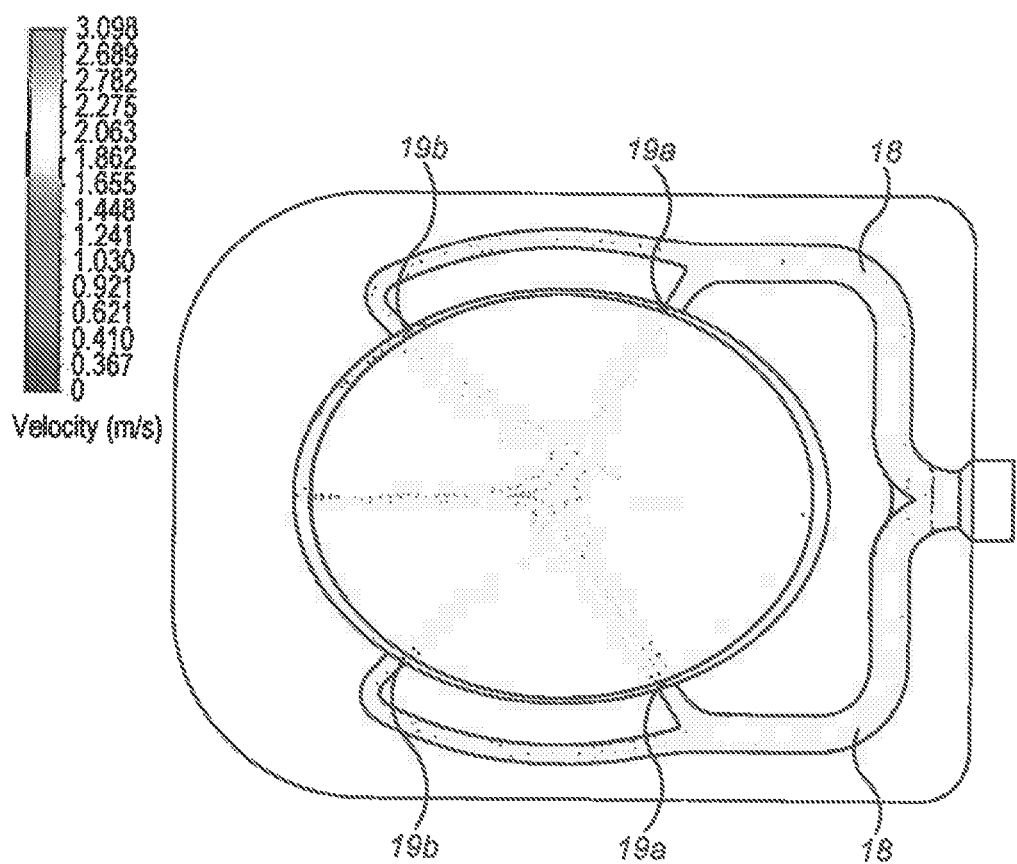
FIG. 5 is a view of the atomiser from above showing a schematic representation of fluid flow.

FIG. 4a shows a representation of the atomiser 5 which includes a light shield or skirt 20. In the embodiment of FIG. 4, fluid enters the atomiser through a single channel which is split into two fluid atomiser channels 18. The single fluid conduit as it enters the atomiser 5 is split around a curved wall on the opposing side to where the fluid conduit enters the atomiser 5. FIG. 4b shows a view of the atomiser 5 from above and shows that the fluid atomiser channels 18 have a first diameter to the point of the first set of fluid outlets 19a and a second diameter to the second set of fluid outlets 19b. The embodiment of FIG. 4b has two fluid atomiser channels 18 and four fluid outlets 19a and 19b. FIG. 4c shows a cross section of the atomiser along axis D-D as shown in FIG. 4b. This cross-section shows the fluid conduit entering the atomiser 5 and the two fluid outlets 19a and 19b. FIG. 4d shows a cross section of the atomiser along axis C-C as shown in FIG. 4b. This cross-section shows the fluid atomiser channels 18 at the second diameter and the first set of fluid outlets 19a.

In certain embodiments, the fluid atomiser channel(s) 18 are in fluid communication with the fluid conduit portion 17. In one embodiment, the atomiser comprises a light shield or skirt 20. The light shield or skirt 20 may define a cavity 21. In one embodiment, the fluid outlets 19 may be positioned such that they open into the cavity 21 defined by the light shield or skirt 20. Having the fluid outlets 19, 19a, 19b open into the cavity 21 is advantageous as it ensures that the spray created by the atomiser is focused on the surface of interest contained within the cavity 21. Therefore the light shield or skirt prevents the spray being wasted as it disperses from the fluid outlets 19, 19a, 19b. The light shield or skirt 20 may be made from a material having a 20 to 40 Shore A hardness, more preferably 30 Shore A hardness. In one embodiment, the diameter of the cavity 21 defined by the interior of the light shield or skirt 20 may reduce from the top of the light shield or skirt 20 to the bottom of the light shield or skirt 20. In a further embodiment, as illustrated in FIGS. 3, 4, and 5, the cavity 21 may be oval shaped. In preferred embodiment, the longest diameter of the oval may reduce from about 12 mm to 14 mm at the top of the light shield or skirt 20 to about 8 mm to 10 mm at the bottom of the light shield or skirt 20.

FIG. 5 shows the preferred fluid flow through the fluid atomiser channels. As shown in FIG. 5, the fluid atomiser channels 18 provide a substantially equal distribution of fluid at each of the fluid outlets 19.

Figure 6:
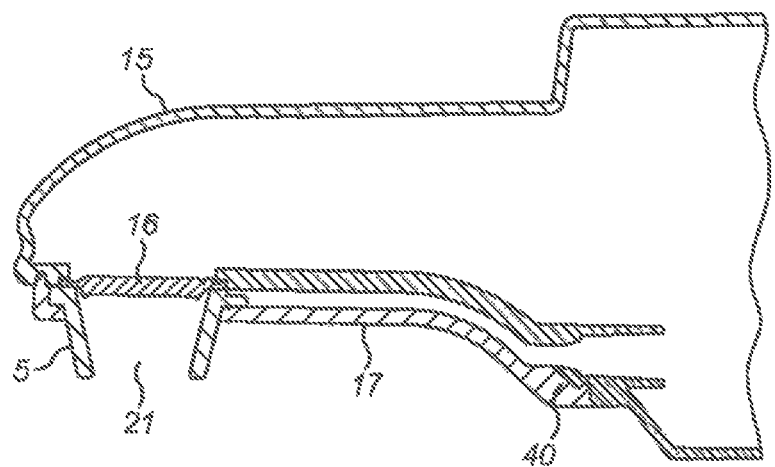
FIG. 6 is a cross-sectional view through Section B-B of the applicator portion shown in FIG. 1.

FIG. 6 shows a schematic representation of the assembled reversibly removable reversibly removable applicator portion 6 attached to the body portion 7. The atomiser 5 sits within the receptacle formed by the fluid conduit portion 17 and is sandwiched between the receptacle and the clear window portion 16. The atomiser 5 is further secured by the applicator housing portion 15. In one embodiment, the fluid conduit portion 17 comprises an enclosure 40 for a fluid orifice of the fluid dispensing means 4. In a preferred embodiment, the enclosure 40 couples to the body portion 7 by a tongue and groove arrangement. The tongue and groove arrangement may be used to prevent fluid from the oral cavity entering and contaminating the device. In a more preferred embodiment, the enclosure 40 couples to the body portion 7 using a Luer slip locator. A Luer slip locator may ensure that the orifice of the fluid dispensing means 4 is sealed by the applicator portion such that it will not leak.

Figure 7:
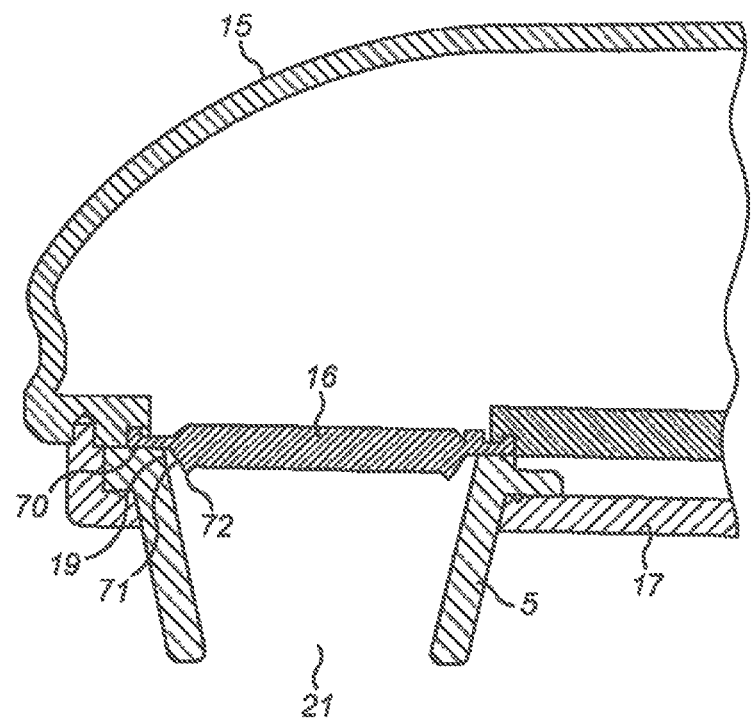
FIG. 7 is a cross-section view of the distal end of the applicator portion shown in FIG. 6.
Figure 8:
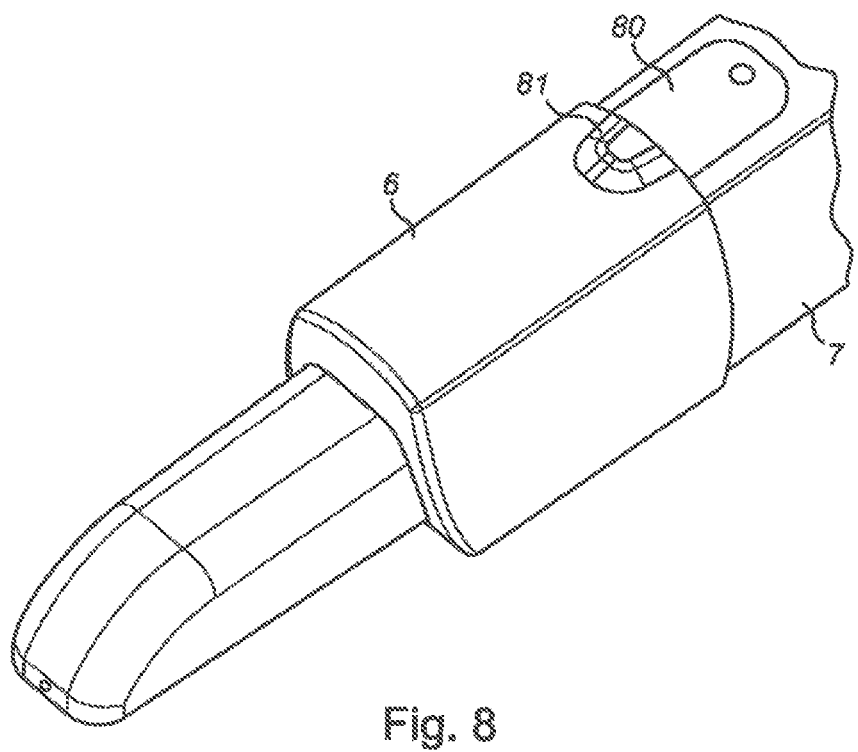
FIG. 8 is a perspective view of the applicator portion attached to the body portion by a clip system.

As shown in FIG. 7, the joints between the components of the reversibly removable atomiser portion 6 may comprise contingency sealing lips 70 that aid in securing the components together. The contingency sealing lips 70 may be made from a hard plastic. The contingency sealing lips 70 provide a dampening effect when the parts are compressed together during use.

As shown in FIGS. 6 and 7, in one embodiment of the invention, the clear window portion 16 may protrude at least partially into cavity 21. As shown in FIG. 7, the protruding portion of the clear window 16 may be angled to form a deflecting surface 71. The angle of the deflecting surface 71 may be such that fluid exiting from fluid outlets 19 will be deflected as it hits the deflecting surface 71. This deflection of the fluid exiting the fluid outlets 19 will increase atomisation of the fluid and aid creation of the spray of the disclosing substance. To prevent the spray from coating the entire surface of the clear window portion 16, the surface of clear window portion 16 in the same plane of the surface of interest may be indented from the deflecting surface 71, thereby forming a lip 72. Lip 72 protects the surface of the clear window portion 16 from being obstructed by spray from the fluid outlets 19 and the deflecting surface 71. This allows light to be passed unobstructed through the clear window portion 16 and the subsequently to the previously described transparent window portion 11 (not shown in FIG. 7) and, ultimately, to the light detection means 12 (not shown in FIG. 7).

In one embodiment, all or part of the clear window portion is frosted. Making all or part of the clear window portion frosted can control accumulation and/or flow of fluid across the surface of the clear window portion.

FIG. 8 shows the reversibly removable applicator portion 6 coupled to the body portion 7. The reversibly removable applicator portion 6 is secured to the body portion 7 by a clip

81 on the reversibly removable applicator portion 6 which is attached to a catch 80 on the body portion 7.

Figure 9A:
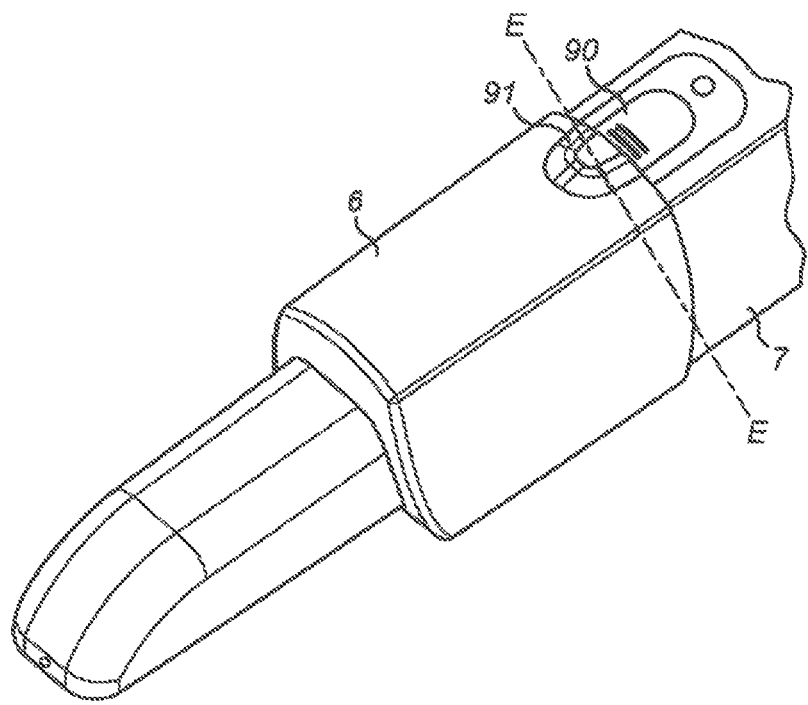
FIG. 9a is perspective view of the applicator portion with an alternate embodiment of the clip system.
Figure 9B:
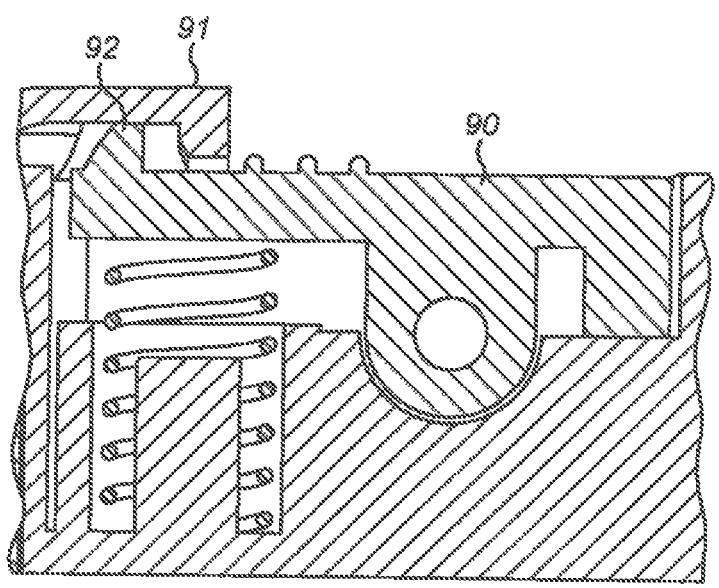

In the embodiment of FIG. 9, catch 90 is shown to be spring loaded and removal of the applicator portion 6 from the body portion 7 after use is achieved by pressing down on catch 90. Pushing down catch 90 disengages the securing tooth 92 from the clip 91 on the reversibly removable applicator portion 6 such that the reversibly removable applicator portion 6 can be pulled from the body portion 7.

Figure 10A:
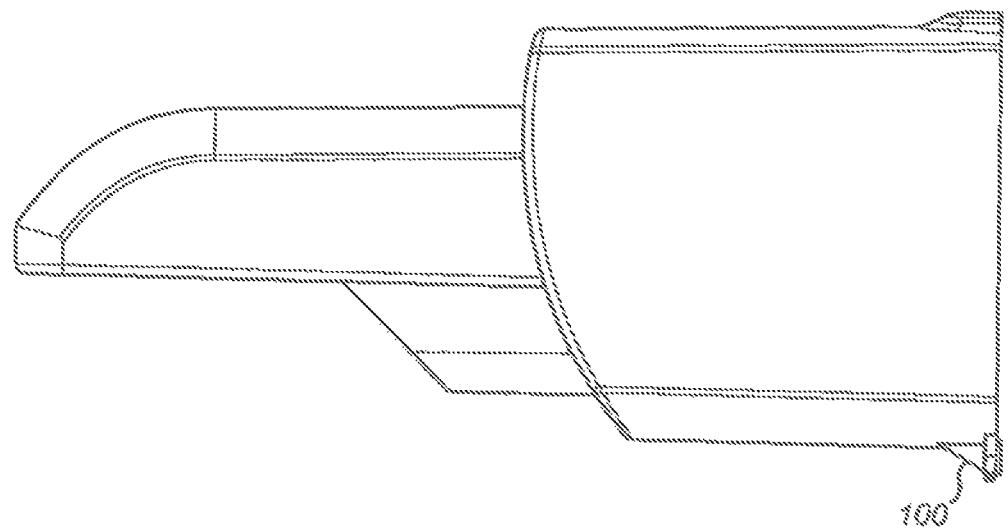
FIG. 10a is a side view of the applicator portion comprising a thumb release catch.
Figure 10B:
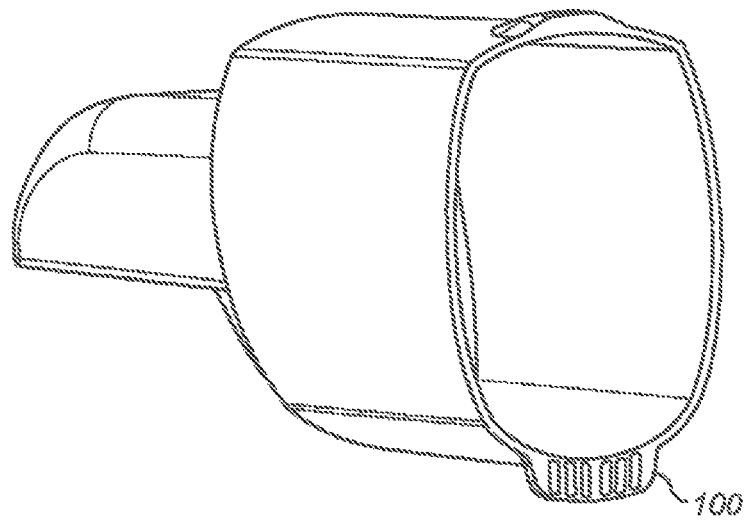
FIG. 10b is a perspective view of the applicator portion comprising a thumb release catch.

In a further embodiment shown in FIG. 10, the reversibly removable applicator portion 6 may have a thumb catch 100 to make removal of the reversibly removable applicator portion 6 easier for the user.

Figure 11:
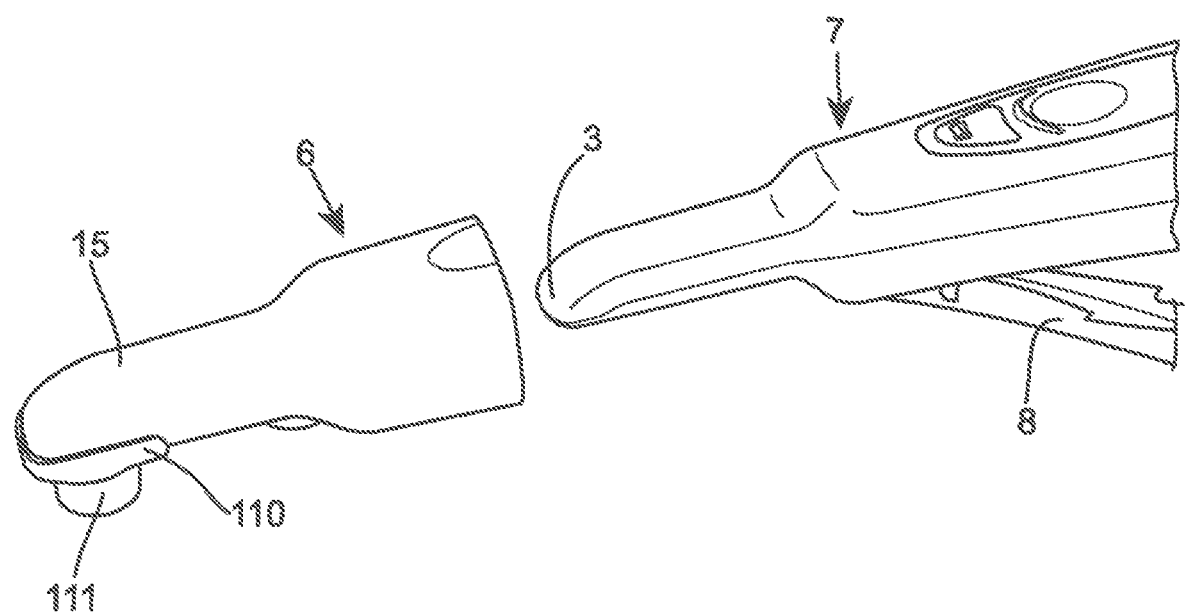
FIG. 11 is a perspective view of a further embodiment of the detection device according to the present invention showing the body portion and applicator portion.

In yet a further embodiment shown in FIGS. 11 to 15, the reversibly removable applicator portion 6 comprises three reversibly interlocking elements. FIG. 11 shows the three elements when coupled together. The first element is the applicator housing portion 15, the second element is a reversibly removable combined atomiser and fluid conduit portion 110, and the third element is a reversibly removable light shield or skirt portion 111.

FIG. 11 also shows this arrangement of elements as it would look prior to being coupled to the distal end 3 of the body portion 7. Also shown in FIG. 11 is the cover 8 for securing the fluid dispensing means.

Figure 12:
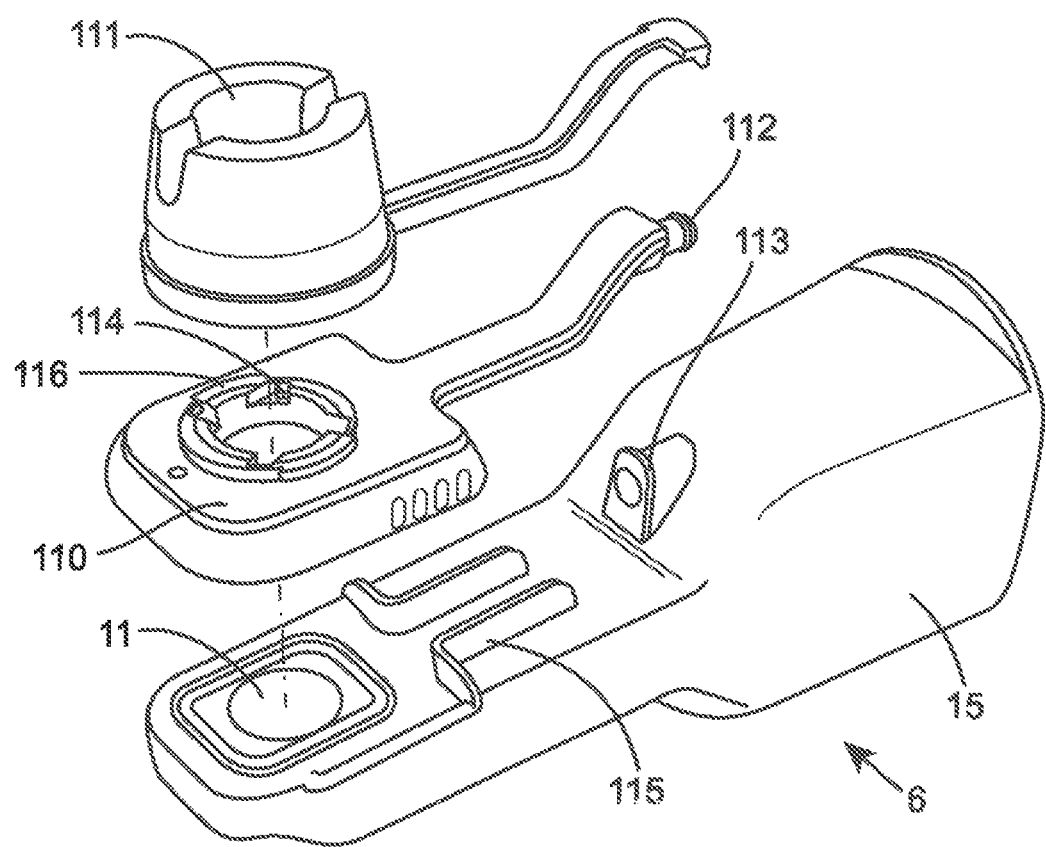
FIG. 12 is a perspective view showing the reversibly removable applicator portion comprising a applicator housing portion, a reversibly removable combined atomiser and fluid conduit portion, and a reversibly removable skirt portion.

FIG. 12 shows an exploded view of the three components of the reversibly removable applicator portion 6 of this embodiment. The three elements of the reversibly removable applicator portion 6 are stacked in order above each other.

Figure 14:
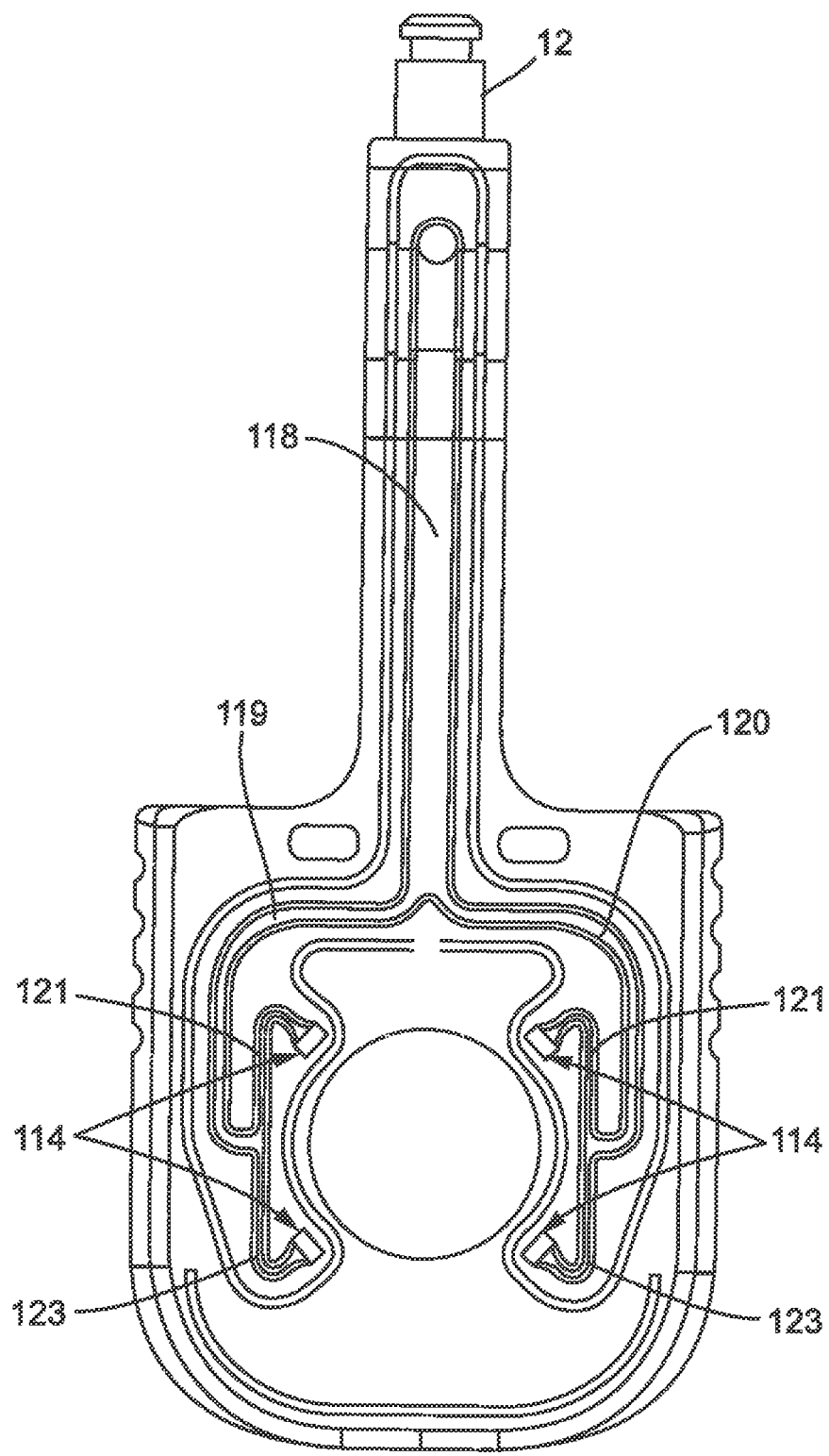
FIG. 14 is a view of the internal structure of the reversibly removable combined atomiser and fluid conduit portion.

The first element of the reversibly removable applicator portion 6 in this embodiment is the applicator housing portion 15 and is shown in FIG. 14 as comprising the transparent window 11, which may be welded into place in this embodiment, the female connector 113 for forming a fluid channel from the fluid dispensing means, and the slidable connector fitting 115 for securing the reversibly removable combined atomiser and fluid conduit portion 110 to the applicator housing portion 15.

The second element of the reversibly removable applicator portion 6 in this embodiment is the reversibly removable combined atomiser and fluid conduit portion 110 and this is shown in FIG. 14 as comprising a male connector 112 for connecting to a female connector on the applicator housing portion 15 to form a fluid conduit to allow passage of fluid from the fluid dispensing means 10 to at least one fluid outlet or a plurality of fluid outlets 114. The reversibly removable combined atomiser and fluid conduit portion 110 also comprises a light shield or skirt connector fitting 116 to allow for connection to the reversibly removable light shield or skirt portion 111.

The third element of the reversibly removable applicator portion 6 in this embodiment is the reversibly removable light shield or skirt portion 111 which comprises a light shield or skirt connector arm 117. The light shield or skirt provides a light shield that prevents incidental light from creating background noise which may interfere with the detection of bioluminescent light emitted from the disclosing substance.

Figure 13:
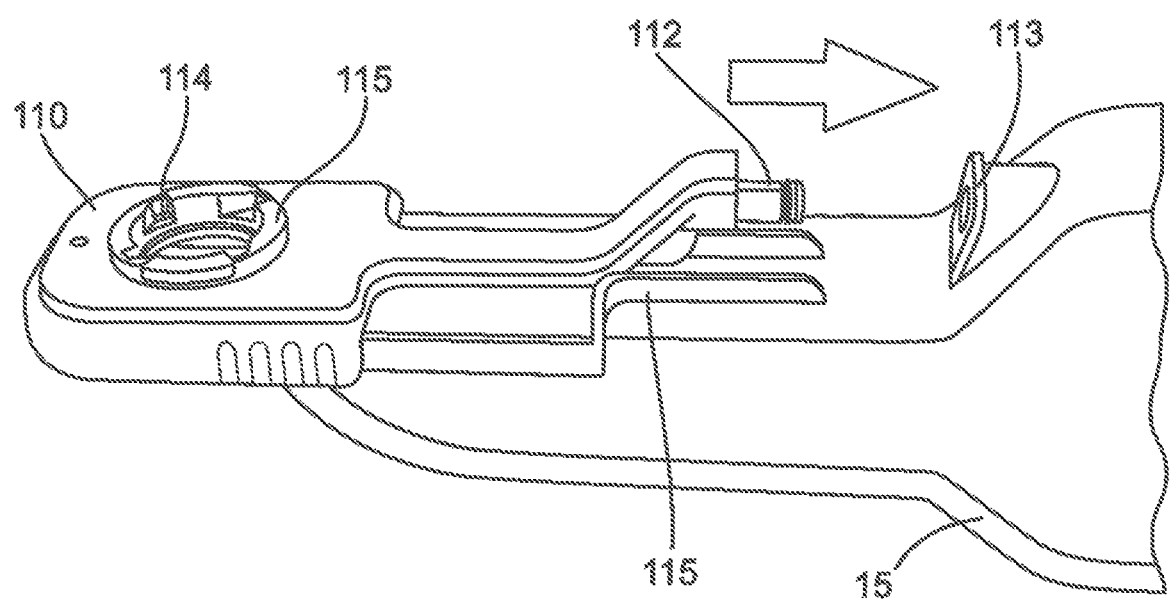
FIG. 13 is a perspective view of reversibly removable combined atomiser and fluid conduit portion being slidably secured on the applicator housing portion.

FIG. 13 shows the reversibly removable combined atomiser and fluid conduit portion 110 being slidably secured to the applicator housing portion 15 and secured by a slidable connector fitting 115. The reversibly removable combined atomiser and fluid conduit portion 110 is also connected and secured to the removable applicator portion by a male connector 112 on the reversibly removable combined atomiser and fluid conduit portion 110 that is inserted into a female connector 113 on the applicator housing portion 15. The connection between the male connector and the female connector creates a fluid conduit that allows fluid that is dispensed from the fluid dispensing means to enter the reversibly removable combined atomiser and fluid conduit portion 110 and flow to fluid outlets 114 from which it can be dispensed onto a surface of interest.

As also shown in FIG. 13, the reversibly removable combined atomiser and fluid conduit portion 110 also comprises a light shield or skirt connector fitting that is adapted to allow the reversibly removable light shield or skirt portion 111 to be secured to the reversibly removable combined atomiser and fluid conduit portion 110.

FIG. 14 shows one embodiment of the internal structure of the reversibly removable combined atomiser and fluid conduit portion 110. The male connector 112 leads to a fluid conduit which in turn splits into at least a first fluid channel 119 and at least a second fluid channel 120. In order to aid equal fluid flow, a protrusion may be formed at the point in which the fluid conduit splits or branches into the at least a first fluid channel 119 and at least a second fluid channel 120. The first and second fluid channels curve around to opposing sides of the cavity into which the fluid is to be sprayed. The fluid channels may further split or branch into smaller fluid atomiser channels 121, 122, 123, 124 that lead to a plurality of fluid outlets 114. In the embodiment shown in FIG. 14, the fluid conduit splits into two fluid channels 119, 120 which each in turn both branch into two further fluid atomiser channels 121, 122, 123, 124 which lead to a total of four fluid outlets 114.

As stated above, the fluid outlets are adapted to provide a substantially equal flow of fluid therefrom. This is advantageous as the equal flow rate of fluid from the plurality of fluid outlets assists in providing an even distribution of the disclosing solution as a spray to the surface of interest. In one embodiment, this can be achieved by positioning the four fluid outlets at substantially equidistant from each other around the circumference of the cavity.

It is envisaged however that there may only be two or three fluid atomiser outlets and corresponding fluid atomiser channels or there may be more than four fluid atomiser channels and corresponding fluid atomiser channels, for example six, seven, eight, nine, ten, or more fluid outlets.

In some embodiments, the diameter of the fluid channels may be larger than the diameter than the fluid atomiser channels. In one embodiment, the diameter of the fluid atomiser channels have a cross sectional area of between about 1 mm$^2$ and about 3 mm$^2$. In a preferred embodiment, the diameter of the fluid atomiser channels have a cross sectional area of about 2 mm$^2$. In another embodiment, the diameter of the fluid atomiser channels have a cross sectional area of between about 0.1 mm$^2$ and about 0.3 mm$^2$. In another preferred embodiment, the fluid atomiser channels have a cross sectional area of about 0.2 mm$^2$.

In one embodiment, the fluid outlets may be 1.5 mm in length and 0.5 mm in width.

Figure 15:
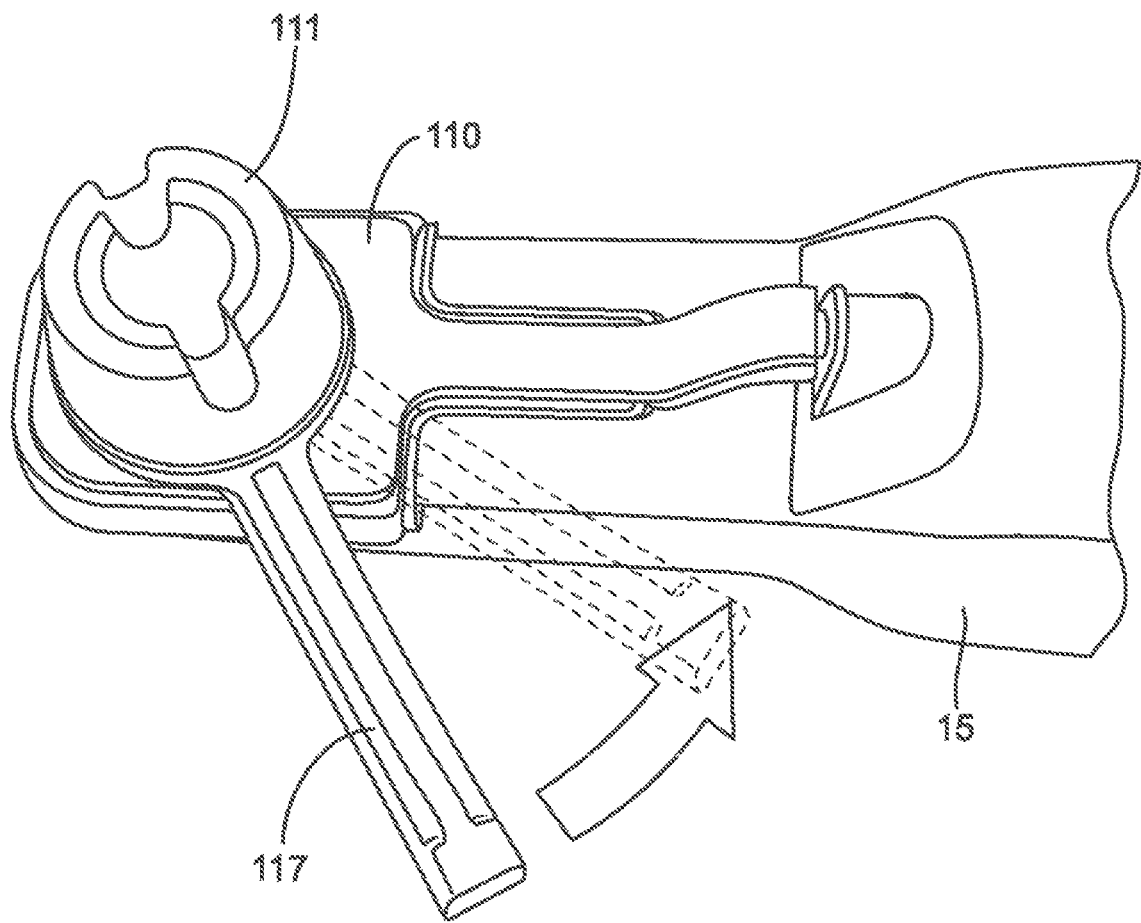
FIG. 15 is a perspective view of the reversibly removable skirt portion being secured to the reversibly removable combined atomiser and fluid conduit portion.

As shown in FIG. 15, in a preferred embodiment, the reversibly removable light shield or skirt portion 111 is secured to the reversibly removable combined atomiser and fluid conduit portion 110 by rotating the reversibly removable light shield or skirt portion 111 either clockwise or counter clockwise such that it locks into place and is held firmly by the light shield or skirt connector fitting 116. In order to aid such locking, the reversibly removable light shield or skirt portion 111 may comprise a light shield or skirt connector arm 117. As shown in FIG. 15, the light shield or light shield or skirt may be circular and have at least one indentation. The light shield or light shield or skirt may be of different sizes in order to best fit over different surfaces, for example, different teeth.

In order to prevent cross contamination between patients, the reversibly removable combined atomiser and fluid conduit portion 110 and the reversibly removable light shield or skirt portion 111 may be disposable and replaceable such that they are only used once and the applicator housing portion 15 my be autoclavable.

Features of the device of this embodiment corresponding to those set out in previous embodiments are described in detail above and are entirely applicable to this embodiment of the device.

The invention claimed is:

1. A detection device for active dental caries and/or tooth erosion, comprising a light detection means, fluid dispensing means, and an atomiser, wherein the fluid dispensing means and atomiser are in fluid communication such that a fluid contained within the fluid dispensing means is dispensed through the atomiser onto a surface of interest,
wherein the detection device further comprises a body portion, comprising a proximal end and a distal end and an applicator portion, wherein the applicator portion is reversibly removable and couples to the distal end of the body portion, wherein the reversibly removable applicator portion comprises the atomiser, wherein the atomiser has a plurality of fluid atomiser channels in fluid communication with a plurality of fluid outlets, wherein each of the plurality of fluid atomiser channels has a first diameter and a second diameter, wherein the second diameter is smaller than the first diameter such that the plurality of fluid outlets are adapted to provide a substantially equal flow of fluid therefrom, wherein the atomiser comprises a light shield or skirt, wherein the light shield or skirt defines a cavity, and wherein at least one fluid outlet opens into a cavity defined by the interior of the light shield or skirt.

2. A detection device according to claim 1, wherein the reversibly removable applicator portion comprises an applicator housing portion, a reversibly removable combined atomiser and fluid conduit portion, and a reversibly removable light shield or skirt portion.

3. A detection, device according to claim 2, wherein the applicator housing portion and the reversibly removable combined atomiser and fluid conduit portion are adapted to be reversibly slidably coupled together.

4. A detection device according to claim 2, wherein the reversibly removable combined atomiser and fluid conduit portion and the reversibly removable light shield or skirt portion are adapted to be reversibly coupled together.

5. A detection device according to claim 2, wherein the reversibly removable combined atomiser and fluid conduit portion comprises a male connector adapted to fit a female connector on the applicator housing portion, wherein the male and female connectors form a fluid conduit in fluid communication with the fluid dispensing means.

6. A detection device according to claim 2, wherein the light shield or skirt is adapted to minimise the amount of ambient light reaching the light detection means.

7. A detection device according to claim 2, wherein the reversibly removable combined atomiser and fluid conduit portion and the reversibly removable light shield or light shield or skirt portion are disposable.

8. A detection device according to claim 2, wherein the atomiser comprises at least four fluid outlets and at least two fluid atomiser channels.

9. A detection device according to claim 1, wherein each of the plurality of fluid atomiser channels has a cross sectional area of between 1 mm$^2$ and 3 mm$^2$.

10. A detection device according to claim 9, wherein each of the plurality of fluid atomiser channels has a cross sectional area of 2 mm$^2$.

11. A detection device according to claim 1, wherein each of the plurality of fluid atomiser channels has a cross sectional area of between 0.1 mm$^2$ and 0.3 mm$^2$.

12. A detection device according to claim 11, wherein each of the plurality of fluid atomiser channels has a cross sectional area of 0.2 mm$^2$.

13. A detecting device according to claim 1, wherein the light shield or skirt is made from a silicone rubber material of a hardness of Shore 20 A to 40 A.

14. A detection device according to claim 13, wherein the silicone rubber material has a hardness of Shore 30 A.

15. A detection device according to claim 1, wherein the light detection means is adapted to detect luminescent light produced from a bioluminescent protein.

16. A detection device according to claim 1, wherein the light detection means is a camera sensor.

17. A detection device according to claim 16, wherein the camera sensor is positioned after a lens array within the body portion.

18. A detection device according to claim 1, wherein the applicator portion comprises a transparent window to allow light to reach the light detection means.

19. A detection device according to claim 18, wherein the body portion comprises a mirror to redirect the light entering the body through the transparent window to the light detection means.

20. A detection device according to claim 18, wherein the transparent window is made from acrylic.

21. A detection device according to claim 18, wherein the transparent window comprises a coating of an anti-mist composition.

22. A detection device according to claim 1, wherein the detection device further comprises a light source.

23. A detection device according to claim 1, wherein the applicator portion comprises a clip for securing the applicator to the body portion.

24. A detection device according to claim 23, wherein the clip corresponds to a catch on the body portion.

25. A detection device according to claim 24, wherein the catch is spring loaded to enable to applicator to be released from the body portion.

26. A detection device according to claim 1, wherein the fluid dispensing means includes a disclosing solution for detecting early stage active caries and erosion.

27. A detection device according to claim 26, wherein the disclosing solution comprises a composition capable of producing an optical signal characteristic of the presence of free ion.

28. A detection device according to claim 27, wherein the disclosing solution is a calcium dependent photoprotein.

29. A detection device according to claim 1, wherein the fluid dispensing means comprises a syringe.

30. A detection device according to claim 29, wherein the fluid dispensing means further comprises a syringe driver means, wherein the syringe driver means is adapted to actuate a plunger of the syringe and expel liquid contained therein.

31. A detection device according to claim 30, wherein the syringe driver means applies a force of 1 to 2 mega Pascal when the detection device is activated.

32. A detection device according to claim 30, wherein the syringe driver means applies a force of 1.5 mega Pascal when the detection device is activated.

33. A detection device according to claim 30, wherein to 40 µl of liquid is expelled from the fluid dispensing when the device is activated.

34. A detection device according to claim 33, wherein 10 µl to 20 µl of liquid is expelled from the fluid dispensing when the device is activated.

35. A detection device according to claim 34, wherein 25 µl of liquid is expelled from the fluid dispensing when the device is activated.

36. A detection device according to claim 29, wherein the syringe is removable from the device.

37. A detection device according to claim 29, wherein the device has a reversibly removable syringe cover.

38. A detection device according to claim 37, wherein the body portion comprises the reversibly removable syringe cover.

39. A kit comprising a detection device according to claim 1.

40. A kit according to claim 39, wherein the detection device comprises a body portion, at least one applicator portion, and at least one syringe.

41. A kit according to claim 39, wherein the kit further comprises instructions for the use of the detection device.

\* \* \* \* \*